(12) United States Patent  
Choe et al.

(10) Patent No.: US 10,786,274 B2  
(45) Date of Patent: Sep. 29, 2020

(54) MICRONEEDLE-BEAUTY DEVICE USING SOUND WAVE VIBRATION

(71) Applicant: EVOSONICS CO., LTD., Wonju-si, Gangwon-do (KR)

(72) Inventors: Jaeyeong Choe, Wonju-si (KR); Sungha Woo, Wonju-si (KR)

(73) Assignee: EVOSONICS CO., LTD, Wonju-si, Gangwon-do (KR)

( * ) Notice: Subject to any disclaimer, the term of this patent is extended or adjusted under 35 U.S.C. 154(b) by 409 days.

(21) Appl. No.: 15/800,018

(22) Filed: Oct. 31, 2017

(65) Prior Publication Data

US 2018/0116687 A1  May 3, 2018

(30) Foreign Application Priority Data

Nov. 1, 2016 (KR) .................... 10-2016-0144168

(51) Int. Cl.
| | |
|---|---|
| *A61B 17/32* | (2006.01) |
| *A61M 37/00* | (2006.01) |
| *A61M 5/46* | (2006.01) |
| *A61H 23/02* | (2006.01) |
| *A61H 39/08* | (2006.01) |
| *A61M 5/32* | (2006.01) |

(Continued)

(52) U.S. Cl.
CPC .. *A61B 17/320068* (2013.01); *A61B 17/3423* (2013.01); *A61H 23/0236* (2013.01); *A61H 23/0245* (2013.01); *A61H 39/08* (2013.01); *A61M 5/3298* (2013.01); *A61M 5/46* (2013.01); *A61M 37/0015* (2013.01); *A61H 2201/0153* (2013.01); *A61H 2201/0157* (2013.01); *A61H 2201/105* (2013.01); *A61H 2201/1685* (2013.01); *A61M 2025/0085* (2013.01); *A61M 2037/0023* (2013.01)

(58) Field of Classification Search
CPC .......... A61M 37/0015; A61M 37/0092; A61M 5/46; A61M 2205/3375; A61M 2210/04; A61B 17/320068

See application file for complete search history.

(56) References Cited

U.S. PATENT DOCUMENTS

| | | | | |
|---|---|---|---|---|
| 7,335,170 | B2* | 2/2008 | Milne | A61H 7/001 |
| | | | | 601/15 |
| 2004/0260212 | A1* | 12/2004 | Cho | A61H 23/0218 |
| | | | | 601/15 |

(Continued)

FOREIGN PATENT DOCUMENTS

| | | | | |
|---|---|---|---|---|
| CN | 1887374 A | * | 1/2007 | |
| EP | 2633882 A1 | * | 9/2013 | .......... A61M 5/3298 |

(Continued)

*Primary Examiner* — Jenna Zhang  
(74) *Attorney, Agent, or Firm* — Revolution IP, PLLC

(57) ABSTRACT

A microneedle skin care device includes a housing having a predetermined space formed therein; a sound wave module disposed inside the housing to provide sound wave vibration; a microneedle assembly configured to receive vibration of the sound wave module and vibrate in front and rear directions, the microneedle assembly having microneedles disposed at a front end; and a needle tip coupled to the front end of the microneedle assembly and having through-holes through which the microneedles selectively pass through formed corresponding to the microneedles.

2 Claims, 7 Drawing Sheets

(51) Int. Cl.
*A61B 17/34* (2006.01)
*A61M 25/00* (2006.01)

(56) References Cited

U.S. PATENT DOCUMENTS

| | | | |
|---|---|---|---|
| 2008/0167590 A1* | 7/2008 | Jon | A45D 34/042 |
| | | | 601/160 |
| 2013/0023806 A1* | 1/2013 | Ungemach | A61H 7/005 |
| | | | 601/114 |
| 2014/0234005 A1* | 8/2014 | Park | A45D 33/36 |
| | | | 401/4 |
| 2015/0045702 A1* | 2/2015 | Lin | A61N 5/0616 |
| | | | 601/19 |
| 2016/0235621 A1* | 8/2016 | Choe | A61H 7/005 |
| 2017/0035649 A1* | 2/2017 | Choi | A61H 23/02 |

FOREIGN PATENT DOCUMENTS

| | | | |
|---|---|---|---|
| KR | 20100060222 A | * | 6/2010 |
| KR | 101401133 B1 | * | 6/2014 |

* cited by examiner

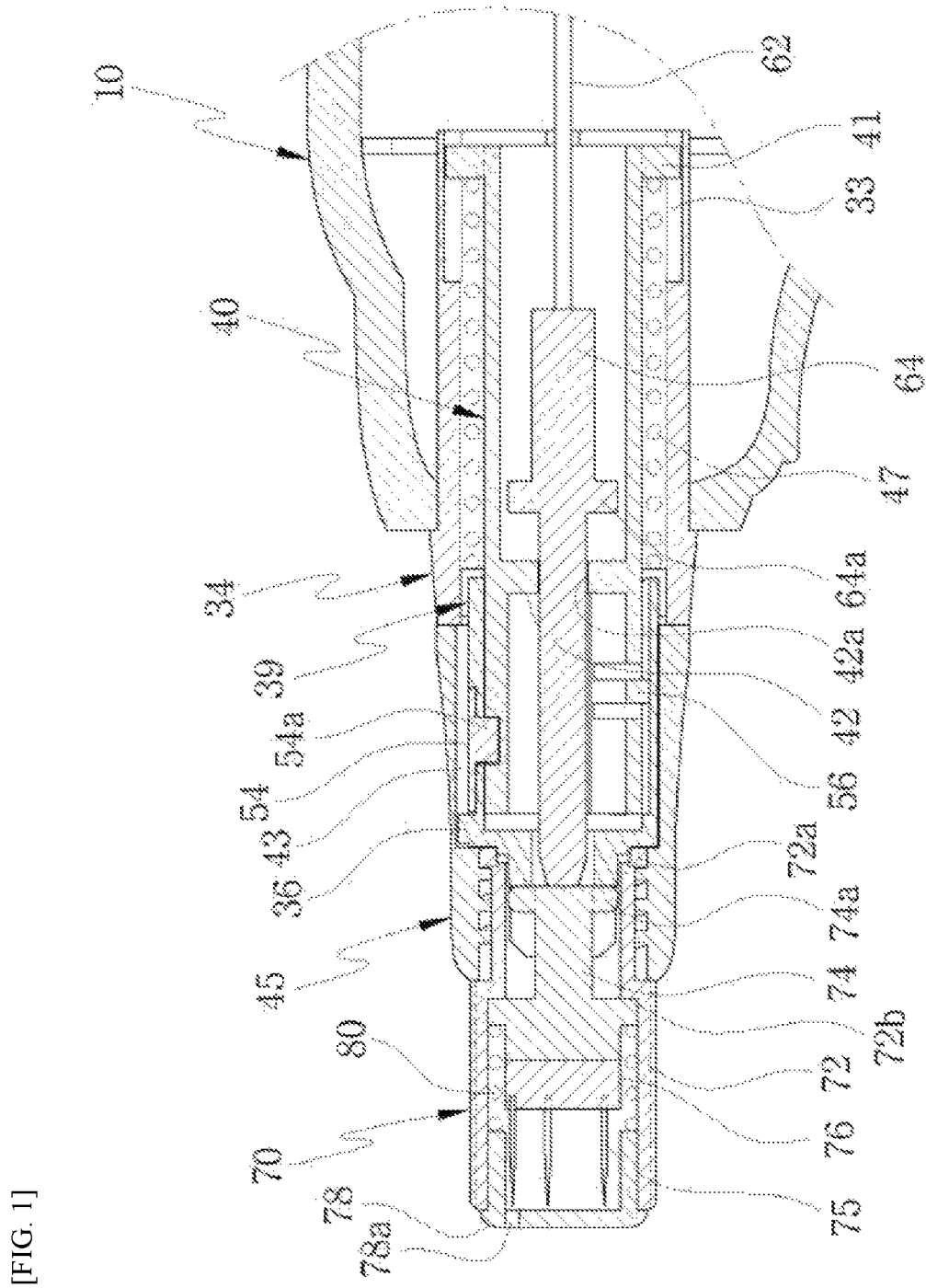
[FIG. 1]

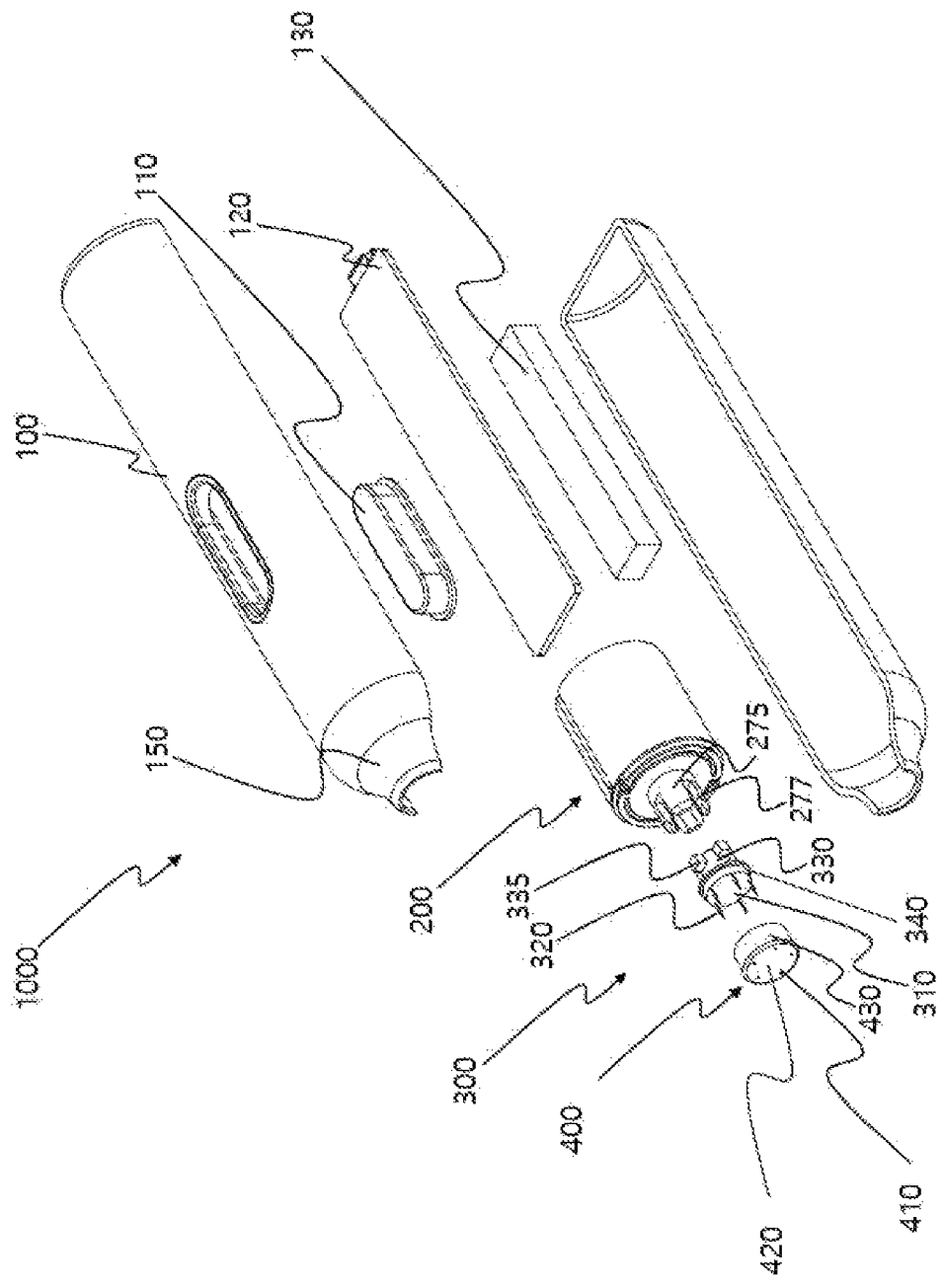
[FIG. 2]

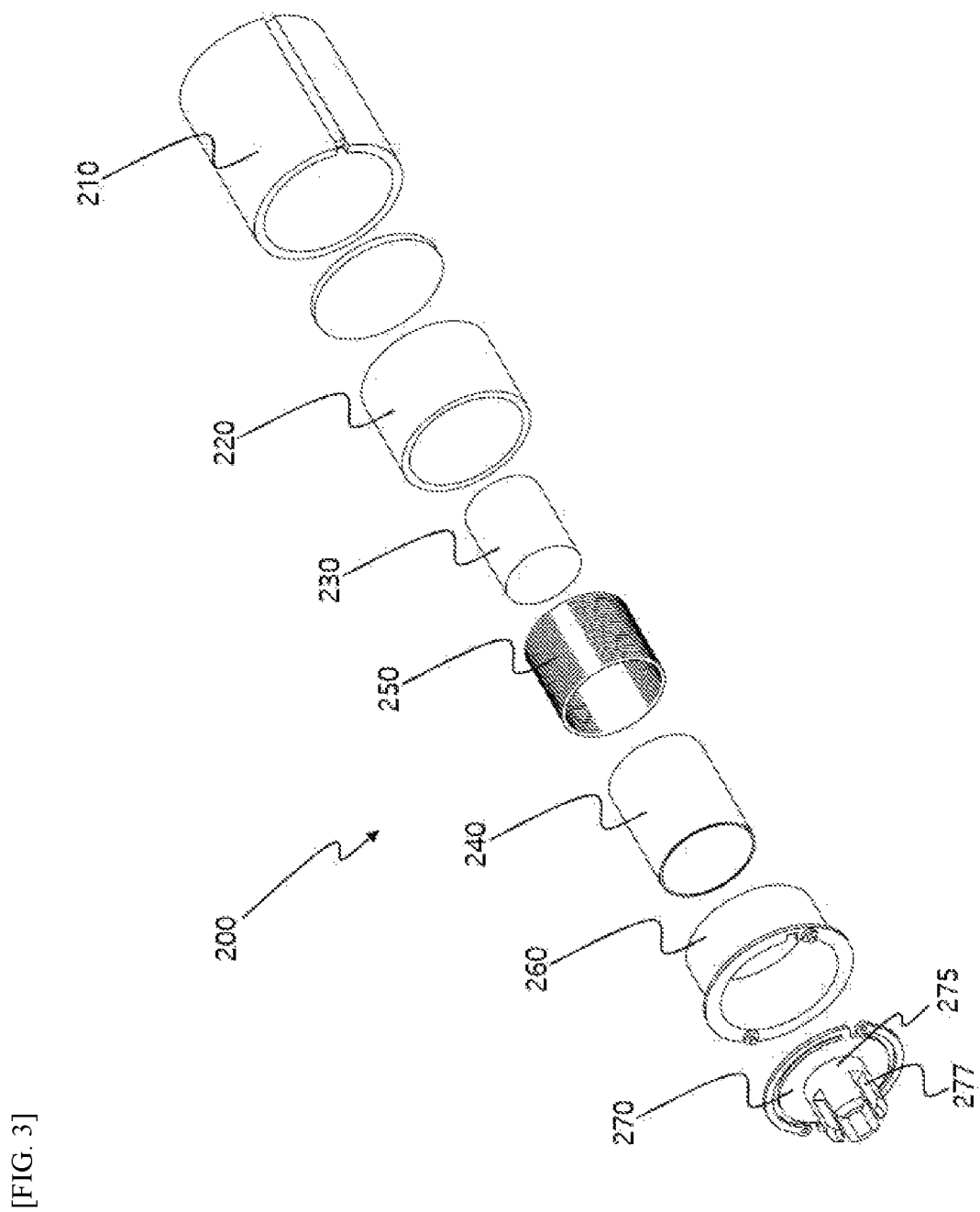
[FIG. 3]

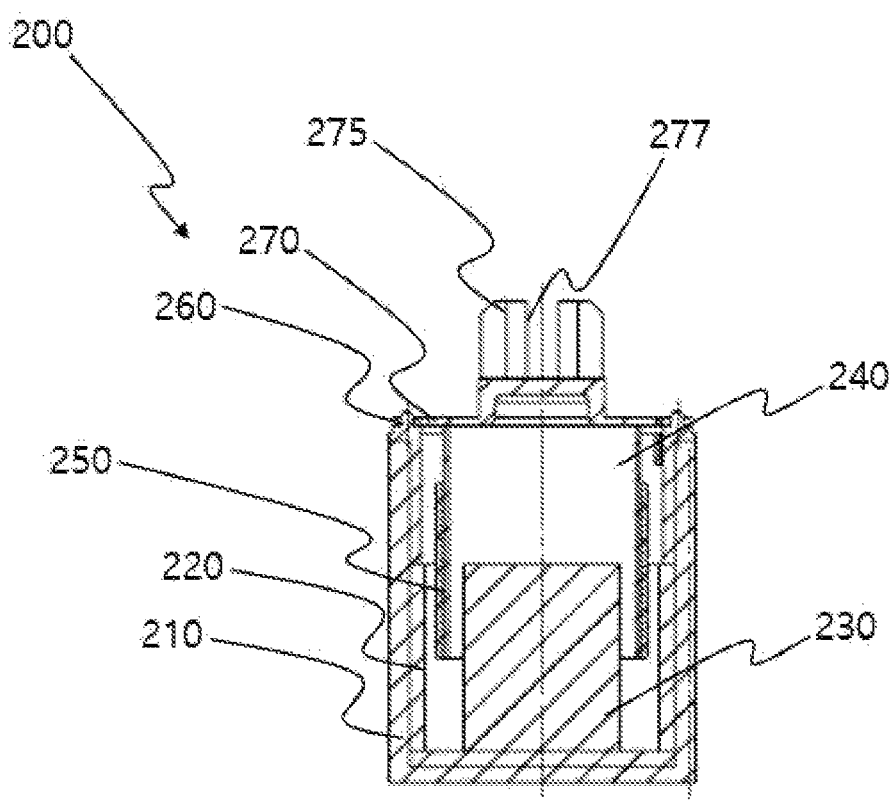
[FIG. 4]

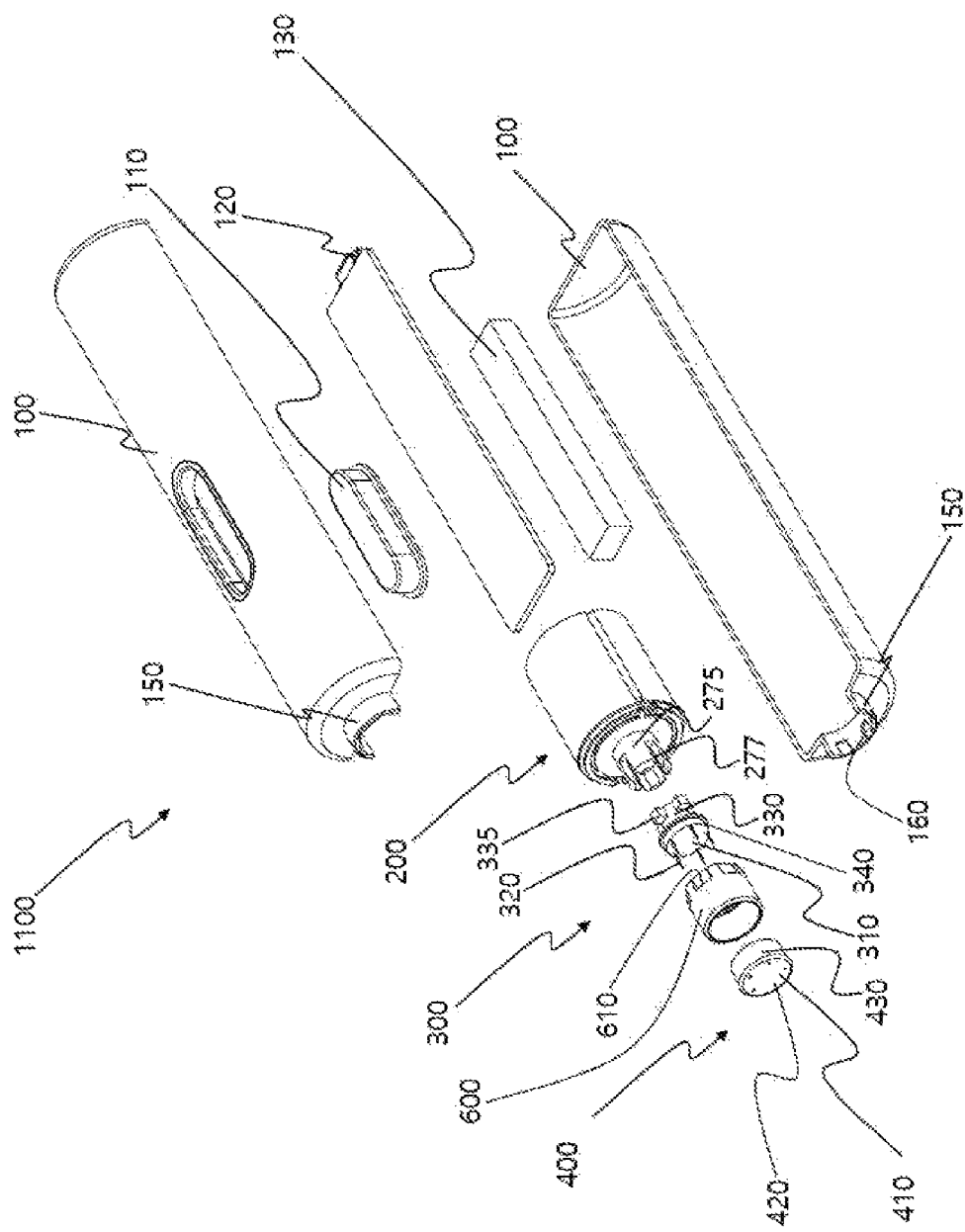
[FIG. 5]

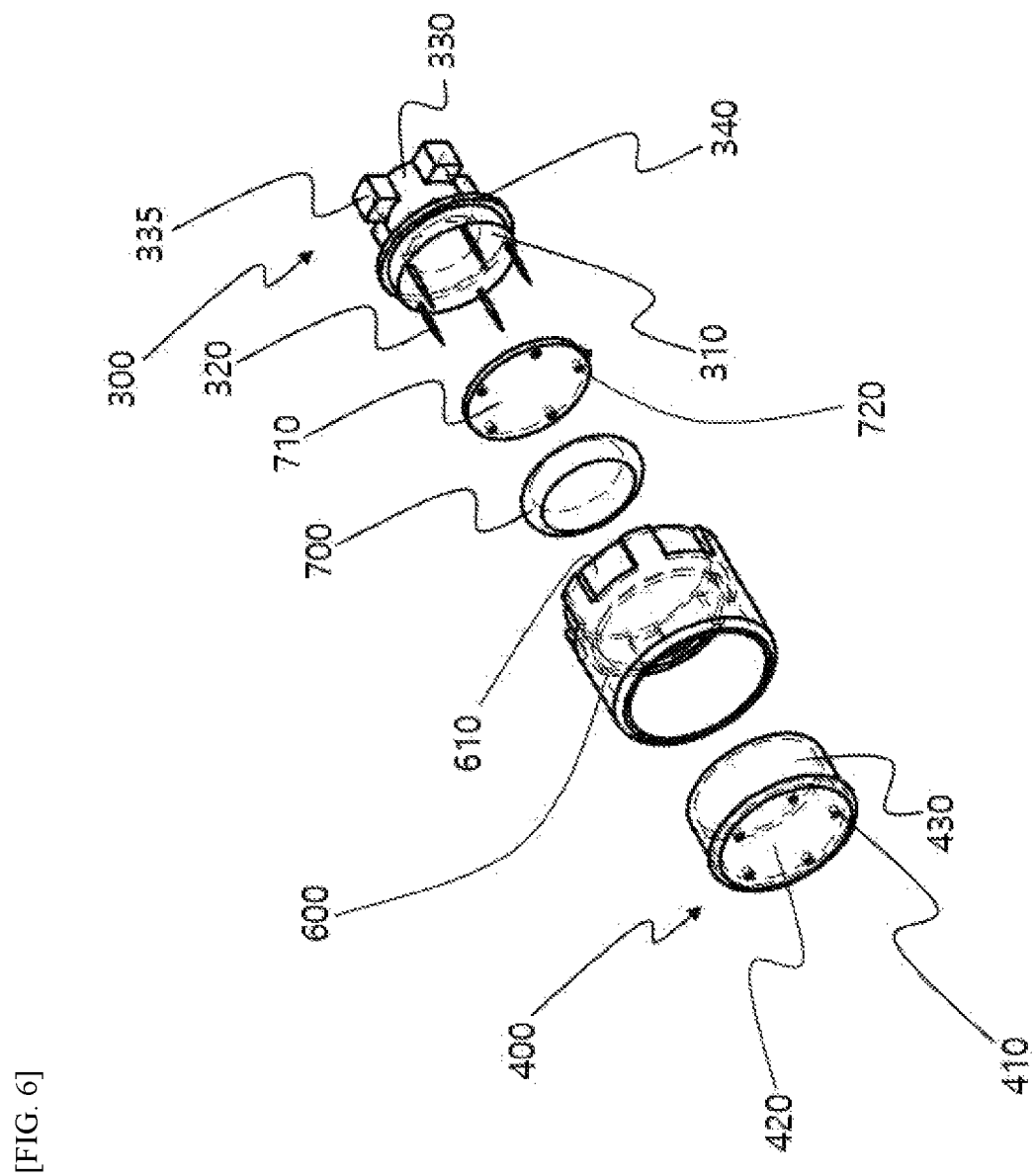
[FIG. 6]

[FIG. 7]
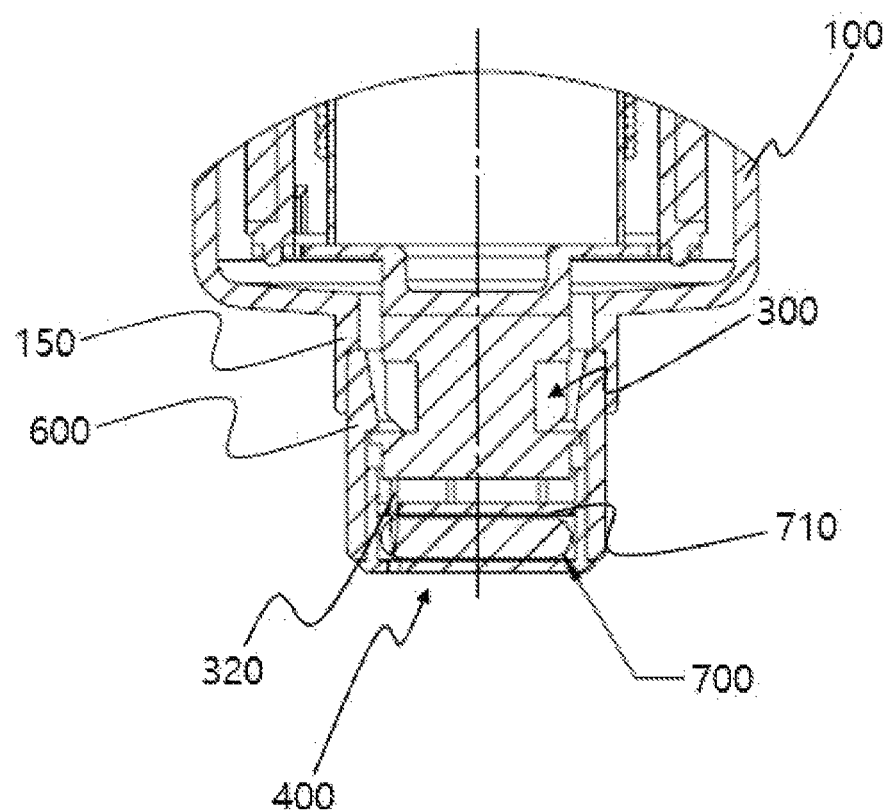

MICRONEEDLE-BEAUTY DEVICE USING SOUND WAVE VIBRATION

CROSS-REFERENCE TO RELATED APPLICATION

This application claims priority to and the benefit of Korean Patent Application No. 10-2016-0144168, filed on Nov. 1, 2016, the disclosure of which is incorporated herein by reference in its entirety.

BACKGROUND

1. Field of the Invention

The present disclosure relates to a microneedle skin care device, and more particularly, a microneedle skin care device for performing skin care by making a wound on the skin through parallel back and forth motion of microneedles and supplying nutrients etc. through the wound.

2. Discussion of Related Art

Generally, a microneedle device is a means of a treatment in which an arbutin/placenta ampoule is penetrated directly into the epidermis and dermis of the skin using needles that are thinner and harder than hair, thereby exhibiting an excellent self-collagen-producing effect, being highly effective in improving elasticity and reducing fine lines, and exhibiting a skin-whitening effect. The treatment may be referred to as a cell restoration treatment that induces self-collagen production without removing or causing damage to the epidermis. By this treatment, scars become shallow by the dermis tissue being newly constructed and rearranged due to a natural action of healing wounds generated as the needles penetrate into skin, fine lines are reduced by the skin being tightened, and pigmentation is improved.

Nowadays, the microneedle device is used for skin care due to being effective in treating wrinkles, pigmentation such as stains, pores, scars caused by acne, burn scars, and stretch marks.

Such a microneedle device includes a handle formed in a shape that is easily gripped by an operator or user by hand, a plurality of discs rotatably installed between supports at both sides of a front end of the handle, and a rotating shaft rotatably configured to rotatably couple the plurality of discs to the supports at the front end of the handle.

However, in the above-described roller type microneedle device, because an adhesive is used to fix needles to the discs, fine cracks are generated between the needles and insertion grooves even after the needles are fixed, skin tissues or other foreign substances may accumulate in the cracks, and there is a hygiene problem of causing skin troubles.

Also, because each of the discs of the microneedle roller is coupled to the rotating shaft and integrally rotates with the rotating shaft, the needles repeatedly penetrate into the same spots of the skin surface while an operator or user rubs the discs against the skin and reciprocates the discs. Thus, there are problems in that advantageous effects of the treatment is deteriorated and skin is damaged.

For the above, an electronic hitting device illustrated in FIG. 1 is used. Referring to FIG. 1, the hitting device includes a fixing coupler (34) fixed to a front region of a main body (10) and having a fitting end (32) with a rotation preventing groove (31) formed at a front inner peripheral surface and a fitting groove (33) formed at a rear inner peripheral surface; a body (37) having a rotation preventing protrusion (35) formed at a rear to be coupled to the rotation preventing groove (31) so that rotation is prevented and having a fitting protrusion (36) formed to protrude from a front outer peripheral surface; a central connector (39) formed to protrude in a stepped shape from a front of the body (37) and having a fitting protrusion (38) with a cross-shaped fitting groove (38a) integrally formed; a front-rear mover (40) having a coupling protrusion (41) formed at a rear to be coupled to the fitting groove (33) of the fixing coupler (34) to be movable in front and rear directions, having a blocking plate (42) with a communication hole (42a) formed at a central inner peripheral surface, and having a front region coupled to an inner peripheral surface of the central connector (39) as a needle depth adjuster (50); an outer coupling cap (45) having a linear fitting groove (43) to which the fitting protrusion (36) of the central connector (39) is detachably coupled; and a support spring (47) interposed between the fitting end (32) and the coupling protrusion 941) to elastically support the front-rear mover (40). A microneedle device is detachably engaged with the electronic hitting device, and vibration that occurs during front and rear reciprocating motion of the electronic hitting device is used.

However, in such an electronic hitting device, a protruding length of microneedles is adjusted by reciprocating motion in front and rear directions. Because the microneedles have to protrude by within 0.25 mm, precise adjustment is required. There is a problem in that such a precise adjustment is difficult with the electronic hitting device.

SUMMARY OF THE INVENTION

The present disclosure has been devised to solve the above-mentioned problems of the related art, and it is an object of the present disclosure to provide a microneedle skin care device capable of accurately adjusting a protruding length of microneedles using sound wave vibration.

To achieve the above object, there is provided a microneedle skin care device including a housing having a predetermined space formed therein, a sound wave module disposed inside the housing to provide sound wave vibration, a microneedle assembly configured to receive vibration of the sound wave module and vibrate in front and rear directions, the microneedle assembly having microneedles disposed at a front end, and a needle tip coupled to the front end of the microneedle assembly and having through-holes through which the microneedles selectively pass through formed corresponding to the microneedles.

The sound wave module may include a lower case having an open upper portion and an accommodating space formed therein, a side ring having an open upper portion and an open lower portion and installed in the accommodating space of the lower case, a magnetic body fixed and installed at a lower surface of the lower case to generate a magnetic force, a bobbin installed inside the lower case at an upper portion of the magnetic body, a voice coil installed at an outer peripheral surface of the bobbin to interact with the magnetic body, an upper case installed at an upper surface of the bobbin and coupled to an upper surface at an edge of the lower case, a cone damper configured to generate vibration in a vertical direction by interactions between the magnetic body and the voice coil, and a guide disposed at an upper surface of the cone damper and having the microneedle assembly coupled to guide vibration of the microneedle assembly.

The microneedle assembly may include a disc-shaped base plate having a predetermined thickness, a plurality of microneedles vertically coupled to a front surface of the base plate, a coupling portion protruding from a rear surface of the base plate and coupled to the sound wave module, a guide protrusion protruding from an outer peripheral surface of the coupling portion and configured to guide vibration by being inserted into an insertion groove formed in the guide of the sound wave module, and a guide ring protruding from an outer peripheral surface of the base plate.

The needle tip may include a disc-shaped tip plate having the through-holes formed at positions corresponding to those of the microneedles and formed in a predetermined size, and a fixing plate disposed at a rear surface of the tip plate, formed in a shape corresponding to that of a needle coupling portion to which the microneedle assembly is coupled at the front end of the housing, and coupled to the needle coupling portion to fix the needle tip.

The needle tip may include a disc-shaped tip plate having the through-holes formed at positions corresponding to those of the microneedles and formed in a predetermined size, and a fixing plate protruding from a rear surface of the tip plate, and further include a coupling housing formed in a hollow shape, having the needle tip coupled to a front end and the microneedle assembly coupled to the other end, and selectively coupled to a needle coupling portion formed at the front end of the housing, wherein, after use of the microneedles, the coupling housing may be detached to entirely replace the needle tip and the microneedle assembly.

Coupling recessed grooves of corresponding shapes may be formed at an outer surface of the coupling housing and an inner surface of the needle coupling portion of the housing so that the coupling housing is coupled to the housing and fixed and, when the coupling housing is coupled by the coupling recessed grooves, the microneedle assembly and the coupling housing may be coupled to each other to allow the guide protrusion of the microneedle assembly to be inserted into the insertion groove of the sound wave module.

The needle tip may include a disc-shaped tip plate having the through-holes formed at positions corresponding to those of the microneedles and formed in a predetermined size, and a fixing plate protruding from a rear surface of the tip plate, and further include a coupling housing formed in a hollow shape, having the needle tip coupled to a front end and the microneedle assembly coupled to the other end, and selectively coupled to a needle coupling portion formed at the front end of the housing, an ampoule capsule disposed between the coupling housing and the microneedle assembly and filled with an ampoule to be applied to skin, and an ampoule cover fixed to an inside of the coupling housing and configured to fix the ampoule capsule to the inside of the coupling housing.

BRIEF DESCRIPTION OF THE DRAWINGS

The above and other objects, features and advantages of the present disclosure will become more apparent to those of ordinary skill in the art by describing exemplary embodiments thereof in detail with reference to the accompanying drawings, in which:

FIG. 1 is a view illustrating a configuration of a microneedle hitting device according to the related art;

FIG. 2 is an exploded perspective view illustrating a configuration of a microneedle skin care device according to an embodiment of the present disclosure;

FIG. 3 is an exploded perspective view illustrating a configuration of a sound wave module according to an embodiment of the present disclosure;

FIG. 4 is a cross-sectional view illustrating the configuration of the sound wave module according to the embodiment of the present disclosure;

FIG. 5 is an exploded perspective view illustrating a configuration of a microneedle skin care device according to another embodiment of the present disclosure;

FIG. 6 is an exploded perspective view illustrating a partial configuration of the microneedle skin care device according to the other embodiment of the present disclosure; and FIG. 7 is a cross-sectional view illustrating the partial configuration of the microneedle skin care device according to the other embodiment of the present disclosure.

DETAILED DESCRIPTION OF EXEMPLARY EMBODIMENTS

Exemplary embodiments of the present disclosure will be described in detail below with reference to the accompanying drawings so that one of ordinary skill in the art to which the present disclosure pertains can easily practice the present disclosure. However, the present disclosure may be implemented in other various forms and is not limited to the embodiments described herein.

FIG. 2 is an exploded perspective view illustrating a configuration of a microneedle skin care device according to an embodiment of the present disclosure, FIG. 3 is an exploded perspective view illustrating a configuration of a sound wave module according to an embodiment of the present disclosure, and FIG. 4 is a cross-sectional view illustrating the configuration of the sound wave module according to the embodiment of the present disclosure.

According to the present disclosure, a microneedle skin care device 1000 includes a housing 100 having a predetermined space formed therein, a sound wave module 200 disposed inside the housing 100 to provide sound wave vibration, a microneedle assembly 300 configured to receive vibration of the sound wave module 200 and vibrate in front and rear directions, the microneedle assembly 300 having microneedles 320 disposed at a front end, and a needle tip 400 coupled to the front end of the microneedle assembly 300 and having through-holes 410 through which the microneedles 320 selectively pass through formed corresponding to the microneedles 320.

A power button 110, a printed circuit board (PCB) 120 performing electrical control, and a battery 130 for supplying power may be built in the housing 100.

The microneedle assembly 300 reciprocates due to vibration caused by the sound wave module 200. That is, although the microneedles 320 are located in the needle tip 400 in a state in which power is not applied, the microneedles 320 reciprocate and are exposed outside the needle tip 400 when power is applied.

A protruding length of the microneedles 320 may be set to be about 0.25 mm.

As illustrated in FIG. 3, the sound wave module 200 may include a lower case 210 having an open upper portion and an accommodating space formed therein, a side ring 220 having an open upper portion and an open lower portion and installed in the accommodating space of the lower case, a magnetic body 230 fixed and installed at a lower surface of the lower case 210 to generate a magnetic force, a bobbin 240 installed inside the lower case 210 at an upper portion of the magnetic body 230, a voice coil 250 installed at an outer peripheral surface of the bobbin 240 to interact with the magnetic body 230, an upper case 260 installed at an upper surface of the bobbin 240 and coupled to an upper surface at an edge of the lower case 210, a cone damper 270 configured to generate vibration in a vertical direction by interactions between the magnetic body 230 and the voice coil 250, and a guide 275 disposed at an upper surface of the cone damper 270 and having the microneedle assembly 300 coupled to guide vibration of the microneedle assembly 300.

When power is applied to the sound wave module 200, the vibration generated due to the interaction between the magnetic body 230 and the voice coil 250 is transmitted to the cone damper 270, and the cone damper 270 vibrates. Due to the vibration of the cone damper 270, the microneedles 320 reciprocate.

The guide 275 to which the microneedle assembly 300 is coupled is included in the cone damper 270.

As illustrated in FIG. 2, the microneedle assembly 300 may include a disc-shaped base plate 310 having a predetermined thickness, a plurality of microneedles 320 vertically coupled to a front surface of the base plate 310, a coupling portion 330 protruding from a rear surface of the base plate 310 and coupled to the sound wave module 200, a guide protrusion 335 protruding from an outer peripheral surface of the coupling portion 330 and configured to guide vibration by being inserted into an insertion groove 277 formed in the guide 275 of the sound wave module 200, and a guide ring 340 protruding from an outer peripheral surface of the base plate 310.

The microneedle assembly 300 is a portion at which the plurality of microneedles 320 are coupled and vibrate and is directly coupled to the cone damper 270 of the sound wave module 200.

More specifically, the microneedle assembly 300 is coupled so that the coupling portion 330 is inserted into the guide 275 of the cone damper 270, and vibration is guided by the guide protrusion 335, which protrude from the outer peripheral surface of the coupling portion 330, being fitted to the insertion groove 277 recessed and formed in the guide 275.

The microneedle assembly 300 is replaced after one treatment for hygiene.

The microneedle assembly 300 is shielded by the needle tip 400 so as not to be exposed to outside.

The guide ring 340 serves to determine a position at which the needle tip 400 is coupled.

The needle tip 400 may include a disc-shaped tip plate 420 having the through-holes 410 formed at positions corresponding to those of the microneedles 320 and formed in a predetermined size, and a fixing plate 430 disposed at a rear surface of the tip plate 420, formed in a shape corresponding to that of a needle coupling portion 150 to which the microneedle assembly 300 is coupled at the front end of the housing 100, and coupled to the needle coupling portion 150 to fix the needle tip 400.

Because the microneedles 320 are exposed to the outside via the through-holes 410 of the needle tip 400, when being coupled, the needle tip 400 should be assembled such that the microneedles 320 are able to pass through the through-holes 410.

A microneedle skin care device 1100 according to another embodiment of the present disclosure is illustrated in FIGS. 5 and 6. Because the configuration of the microneedle skin care device 1100 according to the other embodiment is the same as that of the microneedle skin care device 1000 except for a method in which the microneedles 320 are coupled, overlapping descriptions will be omitted.

FIG. 5 is an exploded perspective view illustrating a configuration of a microneedle skin care device according to another embodiment of the present disclosure, FIG. 6 is an exploded perspective view illustrating a partial configuration of the microneedle skin care device according to the other embodiment of the present disclosure, and FIG. 7 is a cross-sectional view illustrating the partial configuration of the microneedle skin care device according to the other embodiment of the present disclosure.

According to the microneedle skin care device according to the other embodiment of the present disclosure, the needle tip 400 may include the disc-shaped tip plate 420 having the through-holes 410 formed at positions corresponding to those of the microneedles 320 and formed in a predetermined size, and the fixing plate 430 protruding from the rear surface of the tip plate 420, and further include a coupling housing 600 formed in a hollow shape, having the needle tip 400 coupled to a front end and the microneedle assembly 300 coupled to the other end, and selectively coupled to the needle coupling portion 150 formed at the front end of the housing 100, wherein, after use of the microneedles 320, the coupling housing 600 may be detached to replace the needle tip 400 and the microneedle assembly 300.

In the present embodiment, to facilitate replacement of the microneedle assembly 300, the needle tip 400 and the microneedle assembly 300 are integrally configured by the coupling housing 600, and the needle tip 400 and the microneedle assembly 300 are replaced by detaching the coupling housing 600 from the housing 100.

Coupling recessed grooves 610 and 160 of corresponding shapes may be formed at an outer surface of the coupling housing 600 and an inner surface of the needle coupling portion 150 of the housing 100 so that the coupling housing 600 is coupled to the housing 100 and fixed and, when the coupling housing 600 is coupled by the coupling recessed grooves 610 and 160, the microneedle assembly 300 and the coupling housing 600 may be coupled to each other to allow the guide protrusion 335 of the microneedle assembly 300 to be inserted into the insertion groove 277 of the sound wave module 200.

The coupling recessed grooves 610 and 160 are formed in shapes corresponding to each other to fix the coupling housing 600 so as not to be detached from the needle coupling portion 150. The coupling housing 600 may also be coupled to the needle coupling portion 150 by being forcibly fitted thereinto.

As described above, the microneedle assembly 300 should be coupled so that the guide protrusion 335 is inserted into the insertion groove 277 of the guide 275. Consequently, when the coupling housing 600 is coupled to the coupling recessed grooves 610 and 160, to improve convenience of work, the guide protrusion 335 of the microneedle assembly 300 should be placed so that the guide protrusion 335 is able to be inserted into the insertion groove 277 of the sound wave module 200.

The needle tip 400 may include the disc-shaped tip plate 420 having the through-holes 410 formed at positions corresponding to those of the microneedles 320 and formed in a predetermined size, and the fixing plate 430 protruding from a rear surface of the tip plate 420, and further include the coupling housing 600 formed in a hollow shape, having the needle tip 400 coupled to the front end and the microneedle assembly 300 coupled to the other end, and selectively coupled to the needle coupling portion 150 formed at the front end of the housing 100, an ampoule capsule 700 disposed between the coupling housing 600 and the microneedle assembly 300 and filled with an ampoule to be applied to skin, and an ampoule cover 710 fixed to an inside of the coupling housing 600 and configured to fix the ampoule capsule 700 to the inside of the coupling housing 600.

Referring to FIG. 6, the ampoule capsule 700 may be installed inside the coupling housing 600. That is, the ampoule capsule 700 is disposed between the needle tip 400 and the microneedle assembly 300, and the microneedles 320 are disposed to pass through the ampoule capsule 700.

A medicinal ingredient inside the ampoule capsule 700 may be applied to an operator's face by passing through the through-holes 410 of the needle tip 400 due to vibration of the microneedles 320. After use, the ampoule capsule 700 is also discarded with the coupling housing 600.

Consequently, the medicinal ingredient can be applied to the face simultaneously with the process in which the operator uses the microneedles 320 without a separate task in which the operator applies the medicinal ingredient to the face for skin care, and because the medicinal ingredient is applied to the face with the microneedles 320 in direct contact with the medicinal ingredient, an efficiency in which the medicinal ingredient is absorbed into skin may be improved.

According to the present disclosure, because reciprocating motion of microneedles is controlled using sound wave vibration, a reciprocating distance of the microneedles can be constantly maintained by vibration at a constant frequency.

Also, because the microneedles are operated using sound wave vibration, vibration at a high frequency can be used, and blood circulation in skin can be promoted while mitigating pain of treatment in comparison to conventional microneedle products.

The scope of the present disclosure is defined by the claims below rather than the detailed description, and all changes and modifications derived from the sense and the scope of the claims and their equivalents should be construed as belonging to the scope of the present disclosure.

What is claimed is:

1. A microneedle skin care device using sound wave vibration, the microneedle skin care device comprising:
    a housing having a predetermined space formed therein;
    a sound wave module disposed inside the housing to provide sound wave vibration;
    a microneedle assembly configured to receive the vibration of the sound wave module and vibrate in front and rear directions, the microneedle assembly having microneedles disposed at a front end; and
    a needle tip coupled to the front end of the microneedle assembly and having through-holes formed corresponding to the microneedles through which the microneedles selectively pass through,
    wherein the sound wave module includes:
        a lower case having an open upper portion and an accommodating space formed therein;
        a side ring having an open upper portion and an open lower portion and installed in the accommodating space of the lower case;
        a magnetic body fixed and installed at a lower surface of the lower case to generate a magnetic force;
        a bobbin installed inside the lower case at an upper portion of the magnetic body;
        a voice coil installed at an outer peripheral surface of the bobbin to interact with the magnetic body;
        an upper case installed at an upper surface of the bobbin and coupled to an upper surface at an edge of the lower case;
        a cone damper configured to generate vibration in a vertical direction by interactions between the magnetic body and the voice coil; and
        a guide disposed at an upper surface of the cone damper and being coupled to the microneedle assembly to guide vibration of the microneedle assembly,
    wherein the microneedle assembly includes:
        a disc-shaped base plate having a predetermined thickness;
        the microneedles vertically coupled to a front surface of the base plate;
        a coupling portion protruding from a rear surface of the base plate and coupled to the sound wave module;
        a guide protrusion protruding from an outer peripheral surface of the coupling portion and configured to guide vibration by being inserted into an insertion groove formed in the guide of the sound wave module; and
        a guide ring protruding from an outer peripheral surface of the base plate,
    wherein the needle tip includes:
        a disc-shaped tip plate having the through-holes formed at positions corresponding to those of the microneedles and formed in a predetermined size; and
        a fixing plate protruding from a rear surface of the tip plate, and
    further includes a coupling housing formed in a hollow shape, having the needle tip coupled to a front end and the microneedle assembly coupled to an opposing end, and selectively coupled to a needle coupling portion formed at a front end of the housing,
    wherein, after use of the microneedles, the coupling housing is detached to entirely replace the needle tip and the microneedle assembly,
    wherein:
        coupling recessed grooves of corresponding shapes are formed at an outer surface of the coupling housing and an inner surface of the needle coupling portion of the housing so that the coupling housing is fixedly coupled to the housing; and
        when the coupling housing is coupled by the coupling recessed grooves, the microneedle assembly and the coupling housing are coupled to each other to allow the guide protrusion of the microneedle assembly to be inserted into the insertion groove of the sound wave module.

2. A microneedle skin care device using sound wave vibration, the microneedle skin care device comprising:
    a housing having a predetermined space formed therein;
    a sound wave module disposed inside the housing to provide sound wave vibration;
    a microneedle assembly configured to receive the vibration of the sound wave module and vibrate in front and rear directions, the microneedle assembly having microneedles disposed at a front end; and
    a needle tip coupled to the front end of the microneedle assembly and having through-holes formed corresponding to the microneedles through which the microneedles selectively pass through,
    wherein the sound wave module includes:
        a lower case having an open upper portion and an accommodating space formed therein;

a side ring having an open upper portion and an open lower portion and installed in the accommodating space of the lower case;
a magnetic body fixed and installed at a lower surface of the lower case to generate a magnetic force;
a bobbin installed inside the lower case at an upper portion of the magnetic body;
a voice coil installed at an outer peripheral surface of the bobbin to interact with the magnetic body;
an upper case installed at an upper surface of the bobbin and coupled to an upper surface at an edge of the lower case;
a cone damper configured to generate vibration in a vertical direction by interactions between the magnetic body and the voice coil; and
a guide disposed at an upper surface of the cone damper and being coupled to the microneedle assembly to guide vibration of the microneedle assembly,
wherein the microneedle assembly includes:
a disc-shaped base plate having a predetermined thickness;
the microneedles vertically coupled to a front surface of the base plate;
a coupling portion protruding from a rear surface of the base plate and coupled to the sound wave module;
a guide protrusion protruding from an outer peripheral surface of the coupling portion and configured to guide vibration by being inserted into an insertion groove formed in the guide of the sound wave module; and
a guide ring protruding from an outer peripheral surface of the base plate,
wherein the needle tip includes:
a disc-shaped tip plate having the through-holes formed at positions corresponding to those of the microneedles and formed in a predetermined size; and
a fixing plate protruding from a rear surface of the tip plate, and
further includes: a coupling housing formed in a hollow shape, having the needle tip coupled to a front end and the microneedle assembly coupled to an opposing end, and selectively coupled to a needle coupling portion formed at a front end of the housing,
an ampoule capsule disposed between the coupling housing and the microneedle assembly and filled with an ampoule to be applied to skin; and
an ampoule cover fixed to an inside of the coupling housing and configured to fix the ampoule capsule to the inside of the coupling housing.

* * * * *